United States Patent
Cazaux et al.

[11] Patent Number: 6,046,352
[45] Date of Patent: Apr. 4, 2000

[54] PREPARATION OF 4-CYANO-4'-HYDROXYBIPHENYL

[75] Inventors: Jean-Bernard Cazaux, Aramon; Christine Le Breton, Avignon, both of France

[73] Assignee: Societe d'Expansion Scientifique Expansia, France

[21] Appl. No.: 09/355,909

[22] PCT Filed: Feb. 16, 1998

[86] PCT No.: PCT/FR98/00289

§ 371 Date: Aug. 5, 1999

§ 102(e) Date: Aug. 5, 1999

[87] PCT Pub. No.: WO98/37059

PCT Pub. Date: Aug. 27, 1998

[30] Foreign Application Priority Data

Feb. 18, 1997 [FR] France .................................. 97 01861

[51] Int. Cl.⁷ .................................................. C07C 253/14
[52] U.S. Cl. .......................................................... 558/311
[58] Field of Search ............................................. 558/311

[56] References Cited

U.S. PATENT DOCUMENTS 5,262,052  11/1993  Rossiter et al. ......................... 210/653

FOREIGN PATENT DOCUMENTS 044 759   1/1982  European Pat. Off. .
0047453   3/1982  European Pat. Off. .
2002767   2/1979  United Kingdom .
1596014   8/1981  United Kingdom .

*Primary Examiner*—Joseph McKane
*Attorney, Agent, or Firm*—Bierman, Muserlian and Lucas

[57] ABSTRACT

The invention relates to a preparation process for 4-cyano-4'-hydroxybiphenyl, the process comprising the protection of the aldehyde function of 4-bromo-benzaldehyde, the reaction of the protected 4-bromo-benzaldehyde with p-alkoxyphenyl magnesium halide, the deprotection of the formyl radical of the protected 4-alkoxy-4'-formyl-biphenyl and conversion of the formyl group into cyano and hydrolysis of the alkoxy group of the resulting 4-alkoxy 4'-cyano-biphenyl.

6 Claims, No Drawings

PREPARATION OF 4-CYANO-4'-HYDROXYBIPHENYL

This application is a 371 of PCT application FR98/00289 filed Feb. 16, 1998.

The invention relates to a preparation process for 4-cyano-4'-hydroxybiphenyl. This compound is known as an intermediate and used, for example, in the synthesis of monomers of crystal liquid polymers (GB 2002767) (J. Polym. Sci., Part C: Polymer Letters, Vol. 28, 345–355 (1990); J. Mater, Chem., 1993, 3(6), 633–642) or for the formation of specific polysiloxanes (U.S. Pat. No. 5,262,052).

4-cyano-4'-hydroxybiphenyl can be prepared as described in the Application EP44759 or in J. Mater. Chem., 1933, 3(6), 633–642, by reacting 4-bromo-4'-hydroxybiphenyl with copper cyanide. Another preparation method described in the Application U.S. Pat. No. 5,262,052, consists of reacting di(4-methoxyphenyl)zinc with 4-bromobenzonitrile in the presence of $Ni(PPh3)_4$. The disadvantage of these processes is that they use toxic agents such as copper cyanide. A subject of the invention is a preparation process which does not use a toxic agent such as copper cyanide or which uses less toxic agents than those described in the state of the art.

The invention relates to a preparation process for 4-cyano-4'-hydroxybiphenyl, the process comprising:

protection of the aldehyde function of 4-bromo-benzaldehyde, reaction of the protected 4-bromo-benzaldehyde with p-alkoxyphenyl magnesium halide, deprotection of the formyl radical of the protected 4-alkoxy-4'-formyl-biphenyl and conversion of the formyl group into cyano, and hydrolysis of the alkoxy group of the resulting 4-alkoxy 4'-cyano-biphenyl.

The reactions are preferably carried out under an inert atmosphere. For example, the reactions can be carried out under a nitrogen atmosphere.

The aldehyde function can be protected by the standard methods known to a person skilled in the art. Thus, for example, protection can be carried out by using ethylene glycol, propylene glycol or dimethyl ether as agent.

The protected 4-bromobenzaldehyde can be reacted with a Grignard reagent in an aprotic solvent. The alkoxy group of p-alkoxyphenyl magnesium halide is preferably an alkoxy having at most 5 carbon atoms; the alkoxy group can be, for example, a methoxy or ethoxy group and preferably the methoxy group, and the halide used is preferably the chloride or bromide.

The nature of the deprotection reaction depends on the reagent used for the protection reaction. The deprotection can be a hydrolysis. The conversion of the formyl group into cyano can be carried out by the standard methods known to a person skilled in the art; hydroxylamine can be used as a reagent.

The hydrolysis of the alkoxy group can be carried out without hydrolysis of the cyano group by using an appropriate reagent such as pyridinium chloride.

The following examples are presented to illustrate the above procedures and must in no case be considered as a limit to the scope of the invention.

EXAMPLE 1

Preparation of 2-(4 bromophenyl)-1, 3-dioxolane 40 g (216 mmol) of bromobenzaldehyde, 39 ml (700 mmol) of ethylene glycol, 1.6 g (9.3 mmol) of p-toluene sulphonic acid and 670 ml of toluene are introduced into a 2 l three-necked flask equipped with a Dean-Stark apparatus under nitrogen. The reaction mixture is taken to reflux whilst eliminating the water formed. After 24 hours of reflux, the reaction mixture is hydrolized with a saturated solution of sodium carbonate (240 ml). The organic phase is recovered and washed twice with a saturated solution of sodium chloride (2×160 ml), then concentrated under vacuum. The crude product obtained is distilled under 40 mm/Hg (150–156° C.).

EXAMPLE 2

Preparation of 2-[p-(4-methoxyphenyl)-phenyl]-1,3-dioxolane 0.8 g of magnesium, 1 ml of tetrahydrofurane (THF) and one crystal of iodine are introduced into a 50 ml three-necked flask under nitrogen. The reaction mixture is heated to 40° C. and 4.75 g of 4-bromoanisole in solution in 25 ml of THF is poured in. The reaction mixture is taken to reflux for an hour and a half.

After returning to ambient temperature, this solution is poured onto a mixture of 2-(4-bromophenyl)- 1,3-dioxolane (5 g) in 50 ml of THF in the presence of a catalyst (Pd, 0.25%) whilst maintaining the temperature at 0° C. The reaction mixture is left to return to ambient temperature and the second fraction of catalyst (0.25%) is added. The reaction mixture is then heated at 40° C. for 2 hours. After hydrolysis with 40 ml of water, the recovered aqueous phase is extracted with toluene (2×30 ml). The organic phases are combined and concentrated in order to obtain the desired product.

EXAMPLE 3

Preparation of p-(4-methoxyphenyl)benzonitrile 2.6 g of 2-[p-(4-methoxy phenyl)-phenyl]-1,3-dioxolane, 0.917 g of hydroxylamine hydrochloride, 40 ml of 1.8 M hydrochloric ethanol and 10 ml of ethanol are introduced into a 100 ml three-necked flask under nitrogen. The reaction mixture is heated to reflux for 4 hours then concentrated under vacuum. The residue is taken up in 30 ml of water, then 220 ml of methyl ter-butyl ether (MTBE) is added. The organic phase is separated and the aqueous phase is extracted with MTBE (2×20 ml). The organic phases are combined, washed with a saturated solution of sodium chloride, dried over anhydrous magnesium sulphate and concentrated under vacuum (yield: 75%).

EXAMPLE 4

Preparation of 4-cyano-4'-hydroxybiphenyl 1 g of p-(4-methoxyphenyl)benzonitrile and 3 g of pyridium chloride are introduced under nitrogen into a 50 ml two-necked flask. The mixture is heated at 200° C. for 6 hours then it is left to cool down. 5 ml of pyridine and 5 ml of 1 N hydrochloric acid are poured in at 110° C. The reaction mixture is extracted with chloroform at ambient temperature. The organic phases are collected and washed with water, (2×30 ml), dried over anhydrous magnesium sulphate and concentrated under vacuum. After recrystallization from an ethyl acetate/heptane mixture, the sought product is obtained (yield: 50%).

We claim:

1. A preparation process for 4-cyano-4'-hydroxybiphenyl, the process comprising:

the protection of the aldehyde group of 4-bromo-benzaldehyde, the reaction of the protected 4-bromo-benzaldehyde with p-alkoxyphenyl magnesium halide, the deprotection of the formyl radical of the protected 4-alkoxy-4'-formyl-biphenyl and conversion of the formyl group into cyano, and the hydrolysis of the alkoxy group of the resulting 4-alkoxy 4'-cyano-biphenyl.

2. A process according to claim 1 in which the protection is carried out by using ethylene glycol, propylene glycol or dimethyl ether as agent.

3. A process according to claim 1 in which the reaction of the protected 4-bromobenzaldehyde with a Grignard reagent is carried out in an aprotic solvent.

4. A process according to claim 1 in which the alkoxy group of the p-alkoxyphenyl magnesium halide is an alkoxy having at most 5 carbon atoms, and the halide used is the chloride or bromide.

5. A process according to claim 1 in which the deprotection is a hydrolysis.

6. A process according to claim 1 in which the hydrolysis of the alkoxy group is carried out with pyridium chloride.

* * * * *